United States Patent
Enick et al.

(10) Patent No.: US 6,241,807 B1
(45) Date of Patent: Jun. 5, 2001

(54) SYSTEM FOR RECOVERY OF METALS FROM SOLUTIONS THEREOF

(75) Inventors: Robert M. Enick, Pittsburgh; Eric Beckman, Aspinwall, both of PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/265,319

(22) Filed: Mar. 9, 1999

Related U.S. Application Data

(63) Continuation-in-part of application No. 09/250,537, filed on Feb. 16, 1999, now Pat. No. 6,183,815, which is a continuation-in-part of application No. 08/831,999, filed on Apr. 1, 1997, now Pat. No. 5,872,257, which is a continuation-in-part of application No. 08/233,105, filed on Apr. 1, 1994, now Pat. No. 5,641,887.

(60) Provisional application No. 60/077,462, filed on Mar. 10, 1998.

(51) Int. Cl.$^7$ .................................................. C22B 3/26
(52) U.S. Cl. ................... 75/721; 75/743; 75/744
(58) Field of Search .................... 75/721, 744, 743; 210/634

(56) References Cited

U.S. PATENT DOCUMENTS

| | | | |
|---|---|---|---|
| 4,171,282 | 10/1979 | Mueller | 252/356 |
| 5,246,507 | 9/1993 | Kodama et al. | 148/250 |
| 5,356,538 * | 10/1994 | Wai et al. | 210/634 |
| 5,728,431 | 3/1998 | Bergbreiter et al. | 427/388 |

* cited by examiner

Primary Examiner—Roy King
Assistant Examiner—Tima McGuthry-Banks
(74) Attorney, Agent, or Firm—Conley, Rose & Tayon P.C.

(57) ABSTRACT

A system for recovery of metals from solutions containing dissolved metals. The system includes an apparatus and method for placing supercritical carbon dioxide that contains an extractant in contact with the solution and agitating the two resulting phases. Once the metals are extracted by the extractant, they can be removed from the carbon dioxide phase by depressurization or by reduction by exposure to hydrogen. The extractant preferably comprises a metal binding group, a spacer group and a $CO_2$-philic group.

17 Claims, No Drawings

SYSTEM FOR RECOVERY OF METALS FROM SOLUTIONS THEREOF

CROSS-REFERENCE TO RELATED APPLICATIONS

The present application claims the benefit of provisional application Ser. No. 60/077,462, filed Mar. 10, 1998, entitled System for Recovery of Metals from Solutions Thereof; and is also a continuation-in-part of application Ser. No. 09/250,537, filed Feb. 16, 1999, entitled Method and Composition for Surface Treatment of Metals now issued as U.S. Pat. No. 6,183,810; which is a continuation-in-part of application Ser. No. 08/831,999, filed Apr. 1, 1997, entitled Further Extraction of Metals in Carbon Dioxide and Chelating Agents Therefor, and now issued as U.S. Pat. No. 5,872,257; which is a continuation-in-part of Ser. No. 08/233,105, filed Apr. 1, 1994, entitled Extraction of Metals in Carbon Dioxide and Chelating Agents Therefor and now issued as U.S. Pat. No. 5,641,887. All of the aforementioned applications are incorporated herein in their entireties.

STATEMENT REGARDING FEDERALLY SPONSORED RESEARCH OR DEVELOPMENT

Not applicable.

BACKGROUND OF THE INVENTION

1. Technical Field of the Invention

The present invention relates generally to novel compounds for extracting precious metals from solution, and more particularly to compounds useful for extracting precious metals into supercritical $CO_2$. Still more particularly, the present invention relates to compounds comprising three part molecules in which the head is a ligand that forms a complex with the desired metal, the body is a spacer group, and the tail is a $CO_2$-philic compound that renders the molecule soluble in $CO_2$.

2. Background of the Invention

In recent years, a growing demand for precious metals in high-technology applications and the increasing cost of precious metals has made recovery of these metals very important. To meet these demands, industry is turning to new sources of precious metals such as complex sulfide ores, and recycling precious metals from catalysts and electronic scrap.

Conventional solvent extraction is sometimes referred to as liquid ion exchange extraction or liquid/liquid extraction. This process comprises two steps. In the first, the extraction step, dilute aqueous feed solution which contains the metal ion to be recovered is contacted with an organic diluent or carrier containing an ion exchanger or ligand dissolved therein. The organic carrier is typically a hydrocarbon and is immiscible in water. The resulting metal complex migrates to the organic phase. In the second, the stripping step, the separated "loaded" organic phase is mixed with an aqueous solution of a stripping agent and the procedure is reversed, with the metal ion passing back to the new aqueous phase. Thus, the dilute feed solution is converted into a highly concentrated solution, from which the metal values are more readily recovered. The barren organic phase can then be recycled through the system.

The system described above has serious drawbacks, however, as the organic carrier is not typically environmentally friendly and the large volumes of water contaminated through contact with the carrier create a sizable disposal problem. Hence it is desired to provide a carrier or solvent that is capable of performing the same extraction without the negative environmental ramifications.

Supercritical carbon dioxide is environmentally innocuous, as well as being inexpensive and safe to handle. Carbon dioxide has elicited significant scientific interest over the past 15 years because it is considered a "green" alternative to conventional organic solvents. $CO_2$ is inexpensive (approximately $80/ton, 1–2 orders of magnitude less than conventional solvents), non-flammable, and is not currently regulated as a volatile organic compound (VOC).

Although $CO_2$ possesses distinct advantages as a solvent, it also exhibits three significant disadvantages, which have limited current commercial applications, for the most part, to food processing and polymer foam production. First, use of $CO_2$ (in either the liquid or supercritical state) requires the use of elevated pressures, as the vapor pressure of $CO_2$ at room temperature is over 900 psi. Consequently, design and construction of equipment is significantly more expensive than for 1 atmosphere analogs.

Second, utility costs due to processing with high pressure $CO_2$ can be prohibitively high, in particular those due to gas recompression. Consequently, while it has been suggested that depressurization of a $CO_2$ solution to 1 atmosphere is an easy route to recovery of products, it is not likely that a $CO_2$-based process will be economically viable if extensive depressurization is used to recover dissolved products.

The final significant obstacle to the use of $CO_2$ as a solvent in conventional chemical processes is its low solvent power. Although its solvent power was once suggested to be comparable to that of liquid alkanes, recent research has shown that this generalization is in error. Calculation produces solubility parameters for $CO_2$ of 4–5 cal/cm$^3$ in the liquid state, similar to those of fluorinated materials and slightly lower than those of silicones. It is generally accepted that $CO_2$ will not solubilize significant quantities of polar, high molecular weight, or ionic compounds. The low $CO_2$-solubility of many compounds of interest means that large volumes of $CO_2$ are required in a potential process, further diminishing the chance for favorable economics.

Hence, it is presently desired to provide an environmentally friendly system for recovering precious metals. The system should be cost-effective and non-hazardous. Thus it is further desired to provide an extractant that is capable of complexing with the desired metal(s) and is soluble in supercritical or liquid $CO_2$.

BRIEF SUMMARY OF THE INVENTION

The present invention comprises a system for recovering precious metals from acidic solutions thereof. The present system is environmentally friendly, cost-effective and non-hazardous. The present invention comprises dissolving a metal-binding compound (extractant) in carbon dioxide and contacting the $CO_2$ solution with an aqueous solution containing dissolved metals. The aqueous solution is typically an acidic solution in which the metals are present as chlorates. The extractant binds with the metal atoms, transferring them into the $CO_2$ phase. The preferred system further includes recovery of the metals from the $CO_2$ phase by exposure to hydrogen.

The extractants of the present invention comprise highly $CO_2$-soluble molecules that are effective for extracting precious metals from solutions containing the precious metals. The extractant molecules are designed such that they exhibit miscibility with $CO_2$ at moderate pressures, and the resulting complexes between the extractant and the metals in question also exhibit miscibility with $CO_2$ at moderate pressures.

The extractants of the present invention contain certain metal binding groups that contain oxygen, nitrogen or sulfur. These metal binding groups are protonated when the $CO_2$-phase in which they are dissolved is placed in contact with an acidic aqueous phase, as is the case during the extraction of precious metals from HCl-based leach solutions. The protonated extractants can then bind the precious metal anions (of the form $MCl_x^{-2}$ where M is a precious metal such as platinum, gold, palladium, rhodium, etc.) and transfer them from the aqueous phase to the $CO_2$ phase, from which they can be recovered. The metal binding group is selected on the basis of the metal to be recovered and is rendered soluble in $CO_2$ by the addition of a $CO_2$-philic tail. To minimize the effect of the $CO_2$-philic tail on the metal binding group, a spacer group is included in the extractant molecule between the $CO_2$-philic tail and the metal binding group.

DETAILED DESCRIPTION OF THE INVENTION

The present invention comprises $CO_2$-soluble, three-part molecules that can be used to extract precious metals from solutions containing the precious metals. The three parts are: a $CO_2$-philic group, an alkyl spacer (—(CH2)x—), and an organic functional group containing a protonatable nitrogen, oxygen, or sulfur. Compounds having this configuration can be used to extract metal anions of the form $MCl_x^{-2}$ from aqueous solutions.

$CO_2$-philic Groups

To insure high solubility in $CO_2$ at moderate pressures, the extractants include certain functional groups that interact favorably, in a thermodynamic sense, with carbon dioxide. These $CO_2$-philic functional groups include fluoroalkyls (—$CF_2$—), fluoroethers (—$CF_2$—$CF(CF_3)$—O—; —$CF_2$—$CF_2$—O—), silicones (—$Si(R)_2$—O—), phosphazenes (—$P(R)_2$=N—), and alkylene oxides (—$CH_2$—$CH(R)$—O—), where R is a group except hydrogen.

Varying numbers of the $CO_2$-philic groups can be used to render the desired extractant soluble in $CO_2$. According to a preferred embodiment, at least three units of a fluoroether such as hexafluoropropylene oxide are used as the $CO_2$-philic group. In alternative preferred embodiments, at least six units of a silicone functional group, at least six units of a fluoroalkyl functional group, at least three units of a fluorinated polyacrylate functional group, or at least six units of a phosphazene functional group are used. It will nevertheless be understood that more or fewer than these numbers of units can be used without departing from the scope of the present invention.

Spacer Group

The $CO_2$-philic groups preferred in the present invention tend to be strong electron-withdrawing agents. Thus, proximity to the metal binding group mitigates the ability of the metal binding group to perform its intended purpose. Hence, in cases where fluoroethers or fluoroalkyls are used the $CO_2$-philic group, a non-electron withdrawing spacer group is preferably included between the metal binding group and the $CO_2$-philic group. The spacer group is preferably a $(CH_2)_x$ group in which x is preferably at least 3. While as few as 1 or 2 spacer groups can be used, and while there is no particular upper limit on the number of spacer groups, it has been found that fewer than 2 spacer groups do not typically provide sufficient isolation from the electron-withdrawing $CO_2$-philic groups and more than 25 spacer groups render the extractant molecule unnecessarily cumbersome.

Metal Binding Group

As mentioned above, the extractants of the present invention include a head group constituent that can be readily protonated, such as N, O, or S. In general, oxygen-containing solvents can extract gold, while compounds containing nitrogen or sulfur atoms are required to extract platinum and palladium. The protonatable head group constituent is protonated upon exposure of the extractant to the acidic aqueous solution. Once protonated, the extractant molecules bind the precious metal anions in the solution, thereby transferring the metal atoms from the aqueous to the $CO_2$ phase. Alternatively, the metal-binding group can be selected from the oxygen-bearing compounds, such as ketones, ethers, etc., which bind to gold, although they are less preferred as binders for platinum or palladium Recovery of Metals In one type of conventional recovery system, metal ions are leached or dissolved out of ore or mineral waste, resulting in an acidic aqueous solution in which the metals are present as chlorates. According to the present system, a $CO_2$-soluble extractant having a metal binding group selected to bind the desired metal is dissolved in supercritical $CO_2$. The supercritical $CO_2$ is then contacted with the aqueous solution containing the metal to be recovered. Because supercritical $CO_2$ is not miscible with water, a liquid—liquid system is formed. Thorough contact can be ensured by agitating the liquid—liquid system, as is known in the art. The contact results in the capture of the metal by the metal binding group of the extractant and thus transfer of the metal into the $CO_2$ phase.

Once the precious metal anions are extracted into the $CO_2$ phase, the precious metal can be recovered by depressurization of the $CO_2$ followed by reduction of the metal to zero-valent state using conventional methods. A more efficient and thus more preferred method is to reduce the metals while still in solution by exposure to hydrogen. Hydrogen is miscible with carbon dioxide at elevated pressures and its use allows reduction and recovery of the metal without depressurizing the $CO_2$, which in turn leads to savings in utility costs.

The Examples that follow are merely illustrative of currently preferred embodiments and are not intended to limit the present disclosure, the scope of which is commensurate with the claims that follow.

EXAMPLE 1a

Preparation of Tertiary Amine Extractants

A fluoroalkyl-functional $CO_2$-soluble tertiary amine extractant was generated as follows. An amount of 3-(dibutylamino)propylamine was dissolved in previously dry Freon 113 (1,1,2 trichlorotrifluoroethane), to which was then added pyridine at a 1:1 molar ratio to the amine. Subsequently, perfluorooctanoyl chloride, 1:1 molar ratio to the amine, in dry Freon 113 was added while stirring under nitrogen. After stirring at room temperature for several hours, the Freon 113 solution was extracted with water to remove the pyridine hydrochloride byproduct. The solvent was then removed under vacuum and the product recovered in greater than 95% yield. On the IR spectrum the shift of the carbonyl peak from 1776 $cm^{-1}$ (fluoroalkyl acid) to 1720 $cm^{-1}$ shows the formation of the amide linkage.

EXAMPLE 1b

Fluoroether Versions of 1a

Fluoroether carboxylic acids (Krytox functional fluids, DuPont, FSL=2500 molecular weight, FSM=5000 molecular weight, FSH=7500 molecular weight) were first transformed to their respective acid chlorides. For example, the oligomer of hexafluoropropylene oxide, capped at one end with a carboxylic acid group (7500 molecular weight) was transformed to the acid chloride via reaction with thionyl chloride. In a typical reaction, 30 g of 7500 molecular weight fluoroether (4 mmol) and 50 ml. of previously dried perfluorol, 3-dimethyl cyclohexane were added to a reaction flask equipped with a condenser. Subsequently, 0.95 g of thionyl chloride (8 mmol) and 0.58 g of dimethylformamide (8 mmol) were added and the mixture was heated at reflux under a blanket of nitrogen. The residual reactants and DMF are removed via extraction in ether. The solvents in product are removed under vacuum at 75–80° C. The product is characterized by the disappearance of the carboxylic acid peak at 1777 $cm^{-1}$ and the appearance of the acid chloride peak at 1810 $cm^{-1}$ on the FT-IR spectrum and also by the disappearance of the COOH proton at 9.6 ppm on the $^1H$ NMR spectrum.

The fluoroether acid chlorides thus generated are used to synthesize fluoroether-functional tertiary amines as described in 1a, where the fluoroether acid chloride is employed in place of perfluorooctanoyl chloride.

EXAMPLE 1c

Analogs to (1a) With Two $CO_2$-Philic Tails

Versions of 1a and 1b with two $CO_2$-philic tails are synthesized by reacting 3,3'-diamino-N-methyldipropylamine with either perfluorooctanoyl chloride in a 2:1 molar ratio using the same conditions as in 1a, or with one of the fluoroether acid chlorides as in 1b.

EXAMPLE 1d

Analogs to (1a) With Three $CO_2$-Philic Tails

Versions of 1a and 1b with three $CO_2$-philic tails are synthesized by reacting tris(2-aminoethyl)amine with either perfluorooctanoyl chloride in a 3:1 molar ratio using the same conditions as in 1a, or with one of the fluoroether acid chlorides as in 1b.

EXAMPLE 2a

Measurement of Binding of Tertiary Amine Extractants with Platinum Hexachloride $H_2PtCl_6$ was purchased from Aldrich Chemical Co. and dissolved in 0.2M HCl at 1 mg/ml. At the same time, various amounts of the single-tailed fluoroalkyl tertiary amine (1a) were dissolved in 1,1,2 trichlorotrifluoroethane. The two solutions were contacted at an organic:aqueous v/v ratio of 3:7 for several hours while stirring. Following separation of the phases, the concentration of platinum remaining in the aqueous phase was measured using the UV method of Marczenko [9], and compared with the initial level. results are shown below:

| Agent:Pt molar ratio | % extracted |
| --- | --- |
| 0.395 | 9.05 |
| 1.581 | 45.03 |
| 2.767 | 59.84 |
| 3.953 | 97.88 | which shows that the tertiary amines retain their ability to bind platinum anions from solution after functionalization with $CO_2$-philic tails.

EXAMPLE 2b

The experiment as shown in example 2 except that the fluoroether-functional single tail tertiary amine (1b, molecular weight of 5000) was used.

| Agent:Pt molar ratio | % extracted |
| --- | --- |
| .88 | 15.42 |
| 3.52 | 45.03 |
| 6.16 | 76.14 |
| 8.80 | 82.89 | which shows that the fluoroether-functional amines can also bind platinum from aqueous HCl solution.

EXAMPLE 3

Solubility of Complexes of Platinum Hexachloride with $CO_2$-Philic Extractants in $CO_2$ Phase behavior studies of the metal binding group/metal complexes in carbon dioxide were conducted using a high-pressure, variable-volume view cell (D. B. Robinson and Associates). Typically, a known amount of sample (0.3–1.0 g) was added to the top of the quartz tube sample cell along with a number of glass or steel ball bearings to provide mixing. The tube was then sealed inside the steel housing, and a known volume of carbon dioxide was injected into the cell using one of the two Ruska syringe pumps. The quartz sample tube contains a floating piston that separates the sample from the pressure-transmitting fluid, in this study, a silicone oil. The pressure on the sample was raised (via the movement of the piston due to injection of silicone oil by the second Ruska pump) to a point where a single phase was present. Mixing was accomplished by the motion of the ball bearings upon rocking of the entire cell. The pressure was then lowered via slow withdrawal of silicone oil from beneath the piston until the first sign of turbidity appeared, which was indicative of a phase separation. This procedure was repeated until the point of turbidity was known to within 20–30 psi. The corresponding point on the pressure vs. concentration curve was identified as a cloud point. Following identification of the cloud point, an additional amount of measured carbon dioxide was injected into the cell to obtain a new concentration of the chelating agent. The cloud point for this new concentration was measured, and this procedure was repeated until the entire cloud point curve was completed.

Complexes of platinum hexachloride with both the fluoroalkyl-functional tertiary amine and the fluoroether-functional tertiary amine were formed via contact between aqueous and organic solutions. An amount of $H_2PtCl_6$ was dissolved in 0.2 M HCl; an amount of the extractant in question was dissolved in 1,1,2 trichlorotrifluoroethane such that platinum was in considerable excess. The two solutions were contacted with vigorous stirring for 24 hours. After separation of the phases, UV analysis of the aqueous phase showed that the extractant had bound platinum. Consequently, the organic phase was retained and the solvent removed to recover the platinum complex, which was then examined in the Robinson cell as described above.

EXAMPLE 4

A series of effective platinum-binding extractants was made, in which the extractants had the general formula

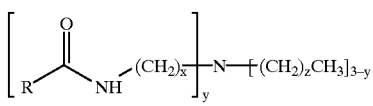

(1)

where R is —$(CF_2)_mCF_3$ where m is preferably 2 to 10 and more preferably about 7, or —$(CF_2CF(CF_3)O)_nCF_2CF_2$ where n is preferably 2 to 25 and more preferably about 14. In the exemplary formulations, x was 3, y ranged from 1 to 3, and z was 3. The subscripts x and z can vary greatly, but each will typically be less than 25 and more preferably less than 10. The extractants made according to formula (1) were each found to bind to platinum and gold to at least a measurable degree.

The foregoing experiments show that it is possible to solubilize platinum complexes of CO2-philic amine extractants in CO2.

EXAMPLE 5

It is expected that extractants having the formula

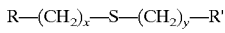

(2)

were R is a $CO_2$-philic group such as a fluoroalkyl, a fluoroether, or silicone as described above, and R' can also be a $CO_2$-philic group, or an alkyl $(CH2)_z$ group (i.e., either R or R' or both can be $CO_2$-philic). In this embodiment, x and y are each preferably greater than or equal to 2, and more preferably 2–4.

EXAMPLE 6

It is further believed that extractants having the formula

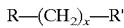

(3)

where R is a $CO_2$-philic group such as a fluoroalkyl, a fluoroether, or silicone as described above, and R' is an ether, ester, ketone, or carboxylic acid group, and x is greater than or equal to 2, preferably 2–4. The oxygen-bearing compounds such as ketones, ethers, etc., bind to gold, but not to platinum or palladium. Hence extractants made according to formula (3) are particularly effective for gold extraction.

What is claimed is:

1. A method for extracting a metal from an aqueous solution containing the metal, comprising:
   (a) dissolving an extractant compound in $CO_2$ to form an extractant solution, wherein the extractant compound comprises a $CO_2$-philic group selected from the group consisting of silicones, phosphazenes, and alkylene oxides;
   (b) contacting the extractant solution with the aqueous solution sufficiently to allow the extractant to capture the metal; and
   (c) removing the metal from the extractant solution.

2. A method for extracting a metal from an aqueous solution containing the metal, comprising:
   (a) dissolving an extractant compound in $CO_2$ to form an extractant solution, wherein the extractant compound comprises a $CO_2$-philic group having the formula —$(CF_2CF(CF_3)O)_nCF_2CF_2$ where n is 2 to 25;
   (b) contacting the extractant solution with the aqueous solution sufficiently to allow the extractant to capture the metal; and
   (c) removing the metal from the extractant solution.

3. A method for extracting a metal from an aqueous solution containing the metal, comprising:
   (a) dissolving an extractant compound in $CO_2$ to form an extractant solution, wherein the extractant compound comprises an alkyl spacer having the formula $(CH_2)_x$ where x is at least 2;
   (b) contacting the extractant solution with the aqueous solution sufficiently to allow the extractant to capture the metal; and
   (c) removing the metal from the extractant solution.

4. A method for extracting a metal from an aqueous solution containing the metal, comprising:
   (a) dissolving an extractant compound in $CO_2$ to form an extractant solution;
   (b) contacting the extractant solution with the aqueous solution sufficiently to allow the extractant to capture the metal; and
   (c) removing the metal from the extractant solution;
   wherein the extractant compound comprises a $CO_2$-philic group, an alkyl spacer having the formula —$(CH_2)_x$—, and a metal-binding group and the $CO_2$-philic group is selected from the group consisting of silicones, phosphazenes, and alkylene oxides.

5. The method according to claim 4 wherein the metal binding group is an organic functional group.

6. The method according to claim 4 wherein the metal-binding group contains a protonatable nitrogen, oxygen, or sulfur.

7. The method according to claim 4 wherein the spacer group comprises $(CH_2)_x$ where x is at least 2.

8. A method for extracting a metal from an aqueous solution containing the metal, comprising:
   (a) dissolving an extractant compound in $CO_2$ to form an extractant solution;
   (b) contacting the extractant solution with the aqueous solution sufficiently to allow the extractant to capture the metal; and
   (c) removing the metal from the extractant solution;
   wherein the extractant compound comprises a $CO_2$-philic group, an alkyl spacer having the formula —$(CH_2)_x$—, and a metal-binding group and the $CO_2$-philic group has the formula —$(CF_2CF(CF_3)O)_nCF_2CF_2$ where n is 2 to 25.

9. The method according to claim 8 wherein the metal binding group is an organic functional group.

10. The method according to claim 8 wherein the metal-binding group contains a protonatable nitrogen, oxygen, or sulfur.

11. The method according to claim 8 wherein the metal-binding group is selected from the group consisting of ethers, esters, ketones, and carboxylic acids.

12. A method for extracting a metal from an aqueous solution containing the metal, comprising:
   (a) dissolving an extractant compound in $CO_2$ to form an extractant solution;
   (b) contacting the extractant solution with the aqueous solution sufficiently to allow the extractant to capture the metal; and
   (c) removing the metal from the extractant solution;
   wherein the extractant compound comprises a $CO_2$-philic group, a metal-binding group and an alkyl spacer having the formula —$(CH_2)_x$— where x is at least 2.

13. The method according to claim 12 wherein the metal binding group is an organic functional group.

14. The method according to claim 12 wherein the metal-binding group is selected from the group consisting of ethers, esters, ketones, and carboxylic acids.

15. The method according to claim 12 wherein the metal-binding group contains a protonatable nitrogen, oxygen, or sulfur.

16. The method according to claim 12 wherein the $CO_2$-philic group has the formula $-(CF_2CF(CF_3)O)_nCF_2CF_2$ where n is 2 to 25.

17. The method according to claim 12 wherein the $CO_2$-philic group is $-(CF_2)_mCF_3$ where m is 2 to 10.

* * * * *